United States Patent [19]
Noe et al.

[11] Patent Number: 6,165,988
[45] Date of Patent: Dec. 26, 2000

[54] MEDICAMENT IN PARTICULATE FORM

[75] Inventors: Christian Noe, Kalterbrunn 7, 4780, Schärding, Austria; Jörg Kreuter, Bad Homburg, Germany; Andreas Zimmer, Frankfurt, Germany; Hans-Peter Zobel, Flörsheim, Germany; Frank Stieneker, Hofheim, Germany; Serap Atmaca-Abdel Aziz, Gross-Gerau, Germany

[73] Assignees: Christian Noe, Schaerding, Austria; Joerg Kreuter, Bad Homburg, Germany

[21] Appl. No.: 08/909,218

[22] Filed: Aug. 11, 1997

Related U.S. Application Data

[63] Continuation of application No. PCT/AT96/00023, Feb. 12, 1996.

[30] Foreign Application Priority Data

Feb. 10, 1995 [AT] Austria ........................................ 248/95
Feb. 9, 1996 [AT] Austria ........................................ 236/96

[51] Int. Cl.⁷ .......................... A01N 61/00; A01N 43/04; A61K 51/00; A61K 9/14
[52] U.S. Cl. .............................. 514/44; 514/1; 424/1.29; 424/1.57; 424/1.37; 424/1.41; 424/1.49; 424/486; 424/78.08; 424/178.1
[58] Field of Search ........................ 514/1, 44; 424/1.29, 424/1.57, 1.37, 1.41, 1.49, 486, 78.08, 178.1

[56] References Cited

U.S. PATENT DOCUMENTS

| | | | |
|---|---|---|---|
| 4,112,215 | 9/1978 | Boessler et al. | 528/503 |
| 4,269,821 | 5/1981 | Kreuter et al. | 424/489 |
| 4,329,332 | 5/1982 | Couvreur | 424/9.6 |
| 4,433,076 | 2/1984 | Bauer et al. | 523/342 |
| 4,705,695 | 11/1987 | Lehmann et al. | 427/2.17 |
| 4,737,357 | 4/1988 | Lehmann et al. | 424/487 |
| 4,940,588 | 7/1990 | Sparks et al. | 424/490 |
| 5,714,166 | 2/1998 | Tomalia et al. | 424/486 |

FOREIGN PATENT DOCUMENTS

| | | |
|---|---|---|
| 0 088 951 A2 | 9/1983 | European Pat. Off. . |
| 0 315 219 A3 | 5/1989 | European Pat. Off. . |
| 0 454 044 | 1/1996 | European Pat. Off. . |
| 1 909 194 | 2/1970 | Germany . |

OTHER PUBLICATIONS

Japanese Patent Abstract JP 59 140 202 A2, dated Aug. 11, 1984.

International Application WO 94/04192 (Lindgren), dated Mar. 3, 1994.

International Application WO 95/16696 (Brunar), dated Jun. 22, 1995.

V. Bentele et al., "Molecular weights of poly(methyl methacrylate) nanoparticles", International Journal of Pharmaceutics, 13 (1983) 109–113.

J. Kreuter: "Encyclopedia of Pharmaceutical Technology", vol. 10, pp. 165–190, 1994, Marcel Dekker, New York.

J. Kreuter (ed.), "Colloidal Drug Delivery Systems", vol. 66 pp. 219–343, Marcel Dekker, New York, 1994.

*Primary Examiner*—Jezia Riley
*Attorney, Agent, or Firm*—Herbert L. Lerner; Laurence A. Greenberg; Werner H. Stemer

[57] ABSTRACT

The medicament in particulate form has one or more anionic or partially anionic active substances bound to a carrier material. The carrier material includes particulate copolymer or homopolymer of acrylic acid or acrylic acid ester or methacrylic acid esters. The carrier further includes oxygen in the ester group, a branched or unbranched alkyl chain with 2–10 carbon atoms, —$NR_2$ where R represents H and lower alkyl chains in any combination, and H or a lower alkyl chain. The grain size distribution of the carrier is 10–1000 nm.

21 Claims, 3 Drawing Sheets

MEDICAMENT IN PARTICULATE FORM

CROSS-REFERENCE TO RELATED APPLICATION

This application is a continuation of copending international application PCT/AT96/00023, filed Feb. 12, 1996.

BACKGROUND OF THE INVENTION

Field of the Invention

The present invention relates to medicinal substances. More specifically, the invention pertains to a medicament in particle form, with one or more anionic or partially anionic active ingredients, preferably nucleic acids, oligonucleotides, proteins, peptides, or biological macromolecules, which are bound by ionic interactions to a carrier material that has the following structure

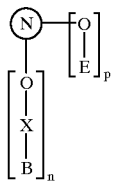

where N=particulate mixed polymer or homopolymer of acrylic 30 acid or acrylate or methacrylates in a molar ratio of p:n from 0:100 to 99:1; O=oxygen of the ester group; X=branched or unbranched alkyl chain with 2 to 10 carbon atoms; B=—$NR_2$ where R=H and low alkyl chains in an arbitrary combination; E=H or low alkyl chain, with a particle size distribution of 10 to 1000 nm. The particles on which the invention is based, whose size is on the order of 10 to approximately 1000 nm, have the object of assuring not only the binding of relevant oligomeric or macromolecular structures but also of protecting them against enzymes that degrade them and of transporting substances purposefully to the site of action and through the cell membrane.

The particles on which the invention is based are synthesized or condensed from suitable monomer building blocks by means of polymerization reactions. Suitable monomers are substances that after the polymerization produce a water-insoluble, physiologically compatible product. Acrylates or methacrylates, with or without basic modifications, are preferably used. Acrylates or methacrylates with basic modifications are distinguished in that the alkyl chains have from 2 to 10 carbon atoms. Chain lengths of 4 to 10 and in particular 5 to 8 carbon atoms should preferably be used, because this assures optimal availability of the basic amino groups for binding the applicable substances.

As the polymerization mechanism, a radical or ionic polymerization in an aqueous or organic phase or a corresponding mixture of water and an organic solvent, such as acetone or ethanol, can be chosen. Once the polymerization is ended and the solvent is removed, the carrier substance can be resuspended in water or preferably in physiologically compatible buffer media.

If a monomer with a protected amino group is used for the condensation, preferably a trifluoroacetyl protective group, then this group can be removed by heating with ammonia in the autoclave. Optionally, a suitable cleaning step, preferably dialysis, can follow.

The carrier materials thus produced are particulate in nature and have a particle size of 10 to 1000 nm; a particle size of 50 to 500 nm and in particular 50 to 300 nm is a preferable goal. Moreover, the carrier material, suspended in water, has a positive surface charge, characterized by a positive Zeta potential.

The carrier material according to the invention is preferably used for binding nucleic acids, such as oligonucleotides, or also peptides, on the basis of ionic interactions.

Compared with existing techniques for binding oligonucleotides, such as antisense oligonucleotides, or binding plasmids that are used for gene transfer and are based on binding the active ingredients to liposomal carriers (lipofectin), the invention has the substantial advantage that compared with liposomal preparations, it is a solid, particulate carrier material with substantially higher stability in aqueous suspensions. In contrast to lipofectin, the carrier material of the invention can be prepared in various forms for various kinds of administration. For example, it can be used in compressed form as an implant, which releases the active ingredient in controlled fashion over a certain period of time, or as an oral form of medicament that can be produced by compression.

Compared with previously used particulate carriers, such as nanoparticles on an alkylcyanoacrylate basis, the invention provides for the advantage that specific functional groups can be incorporated into the polymer structure that assure a targeted binding of the active ingredient on the basis of ionic interactions. In the prior art, particulate carriers developed until now, both on an alkylcyanoacrylate basis and a methacrylate basis, exhibit no binding or only inadequate binding. The previously known nanoparticulate forms of medicament, however, do not have the basic functional groups described in the present invention. A binding of active ingredients to previously known nanoparticles, usually methyl methacrylates, takes place nonspecifically by adsorption effects of lipophilic substances to surfaces or by encapsulation or embedding in the polymer structure.

Particles on an acrylate basis in microparticulate form, which have basic modifications, are also known. Those carrier materials are substantially distinguished from the present invention in that they have a particle size of >1 μm. Such preparations are often used as starting products for producing coatings on tablets or for producing deposition matrix systems for oral or transdermal forms of medication (EP 0 164 669 A2, EP A 0 315 219). Parenteral application in the form of an IV application of such microparticulate carrier materials as an independent form of medication has not been known until now.

Although the invention is illustrated and described herein as embodied in a medicament in particulate form, it is nevertheless not intended to be limited to the exemplary details described, since various modifications and structural changes may be made therein without departing from the spirit of the invention and within the scope and range of equivalents of the claims.

The construction and method of operation of the invention, however, together with additional objects and advantages thereof will be best understood from the following description of specific examples, partly with reference to the appended figures of the drawing.

EXAMPLE 1

Production of a carrier polymer with a 50 mol % basic part.

A monomer solution, comprising 1% methyl methacrylate (MMA) and 1% trifluoroacetylaminohexyl methacrylate monomer in 44% acetone, is polymerized at 63° C. after the start of polymerization by means of a 0.03% ammonium peroxide sulfate solution (APS), while stirring at 400 rpm.

In detail, aqua dem. is boiled out for 1 h with the introduction of nitrogen. 40 g of it and 33 ml of acetone (26.1 g) are placed in a 100 ml screw-lid vessel. At a temperature of 55° C., first trifluoroacetylaminohexyl methacrylate monomer/acetone solution (1:1), MMA, and then 450 µl of APS starter solution (5% concentration) are added. This is then heated to 63° C. and stirred at that temperature for 20 h. After that, the screw lids of the vessels are removed, and stirring is continued at this temperature for another 1.5 h. Finally, the mixture is supplemented to 50 g with aqua dem.

The resultant dispersion is mixed with concentrated ammonia in a proportion of 1:2 (g/g) and autoclaved for 60 minutes at 121° C. After that, dialysis is performed for three days in flowing water and one day in aqua dem.

Figure 1:
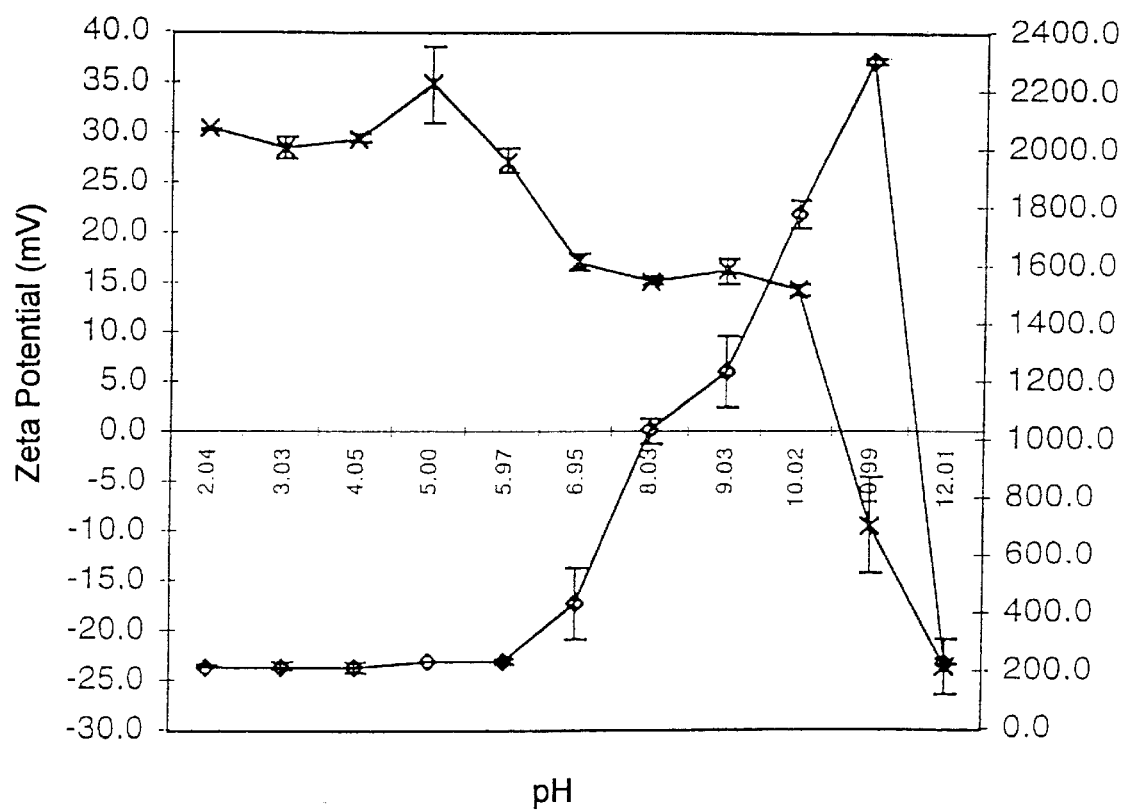
FIG. 1 is a graph showing the Zeta potential and the particle diameter as a function of the pH.

The polymer obtained is then freeze-dried. The particle size and surface charge are dependent on the pH, because of the content of basic groups. By the formation of clumps, particle sizes above the size range of 10–1000 nm deriving from the polymerization can also result (FIG. 1).

EXAMPLE 2

Binding of oligonucleotides.

7.5 mg of the carrier polymer produced in Example 1 are dispersed in 1.0 ml of distilled water with the aid of ultrasound. This produces a 0.75% carrier suspension, of which 60 µl is mixed at room temperature (20° C.) with 30 µl of phosphate buffer (70 mM), pH 7.0. This carrier suspension is mixed with 60 µl of oligonucleotide solution (36.4 µg per ml) and incubated for 2 h at 20° C.

Figure 2:
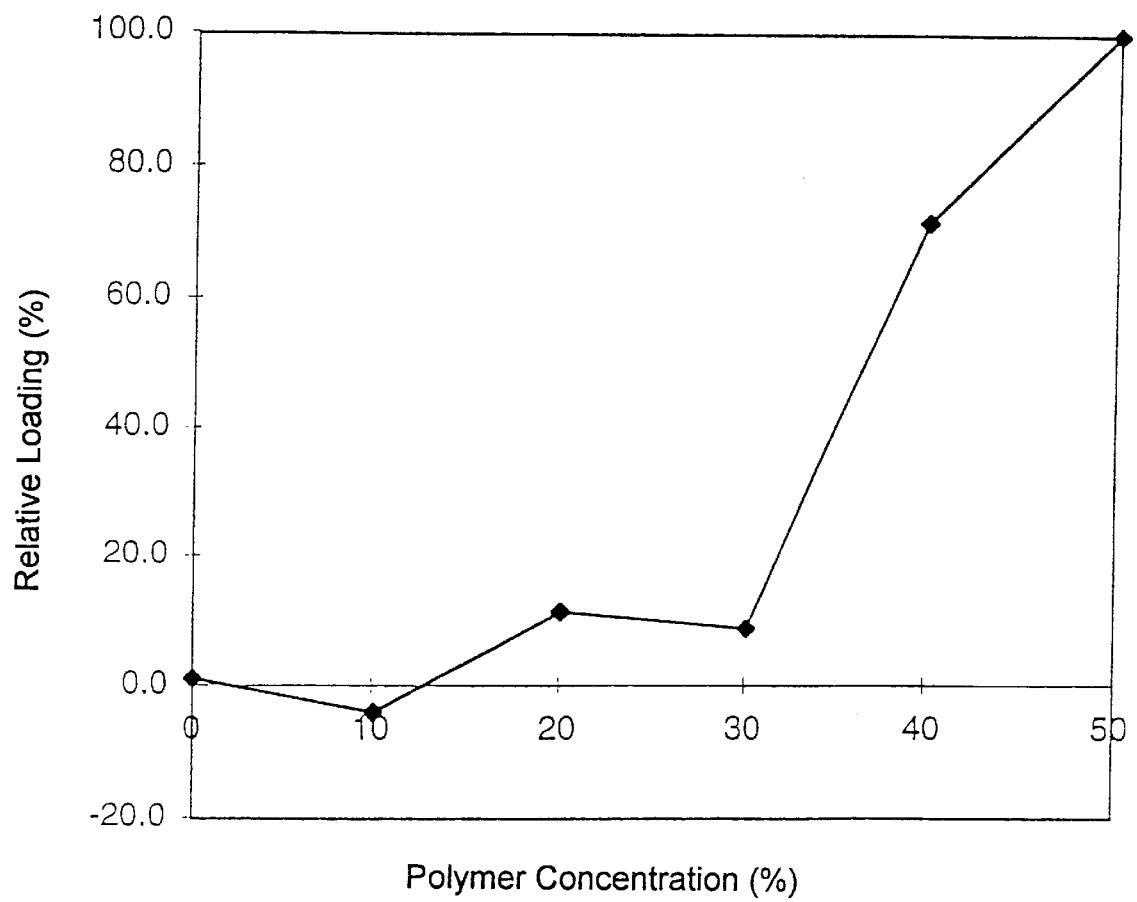
FIG. 2 is a graph showing the relative loading as a function of the copolymer concentration.

To determine the bound proportion of oligonucleotide, 100 µl of this particle suspension are centrifuged off in an ultracentrifuge at approximately 100,000 g in 30 minutes. The non-bound proportion is determined photometrically in the remainder (FIG. 2).

EXAMPLE 3

Binding of peptides, taking TGF α as an example.

20 mg of the carrier polymer produced in Example 1 are dispersed in 1.0 ml of distilled water with the aid of ultrasound. This produces a 2% carrier suspension, of which 125 µl is mixed with 62.5 µl of a 0.3% PBS buffer solution containing BSA, pH 7.4. To this dispersion, there is admixed 62.5 µl of a TGF α solution (30 µg per ml) is admixed, and the mixture is incubated for 24 h at room temperature.

The bound peptide proportion is determined analogously to Example 2. TGF α can be determined using a suitable ELISA test or by measuring the radioactivity remaining on the particle after tagging with $^{125}I$.

On average, 70 to 90% of the quantity of peptide used is bound to the particulate carrier.

EXAMPLE 4

Production of a carrier polymer with a 30% basic part.

A monomer solution, comprising 2.1% methyl methacrylate (MMA) and 0.9% trifluoroacetylaminohexyl methacrylate monomer in 10% acetone, is polymerized at 78° C. after the start of polymerization by means of a 0.03% ammonium peroxide sulfate solution (APS), while stirring at 400 rpm.

Specifically, aqua dem. is boiled out for 1 h with the introduction of nitrogen. 67.5 g of it and 7.5 ml of acetone are placed in a 100 ml screw-lid vessel. At a temperature of 78° C., the monomers and then 450 µl of APS starter solution (5% concentration) are added. Next, this is heated to 63° C. and stirred at this temperature for 20 h. After that, the screw lids of the vessels are removed, and stirring is continued at this temperature for another 1.5 h. Finally, the mixture is supplemented to 75 g with aqua dem.

In addition, dialysis is performed for three days in flowing water and one day in aqua dem. and the polymer thus obtained is subsequently freeze-dried.

EXAMPLE 5

Binding of oligonucleotides.

A dispersion with a concentration of 200 µg/ml of the carrier polymer produced in Example 4 in PBS buffer, pH 7.4, is incubated with increasing concentrations of an oligonucleotide (10 to 100 µg/ml in PBS), for three hours at room temperature (20° C.)

Figure 3:
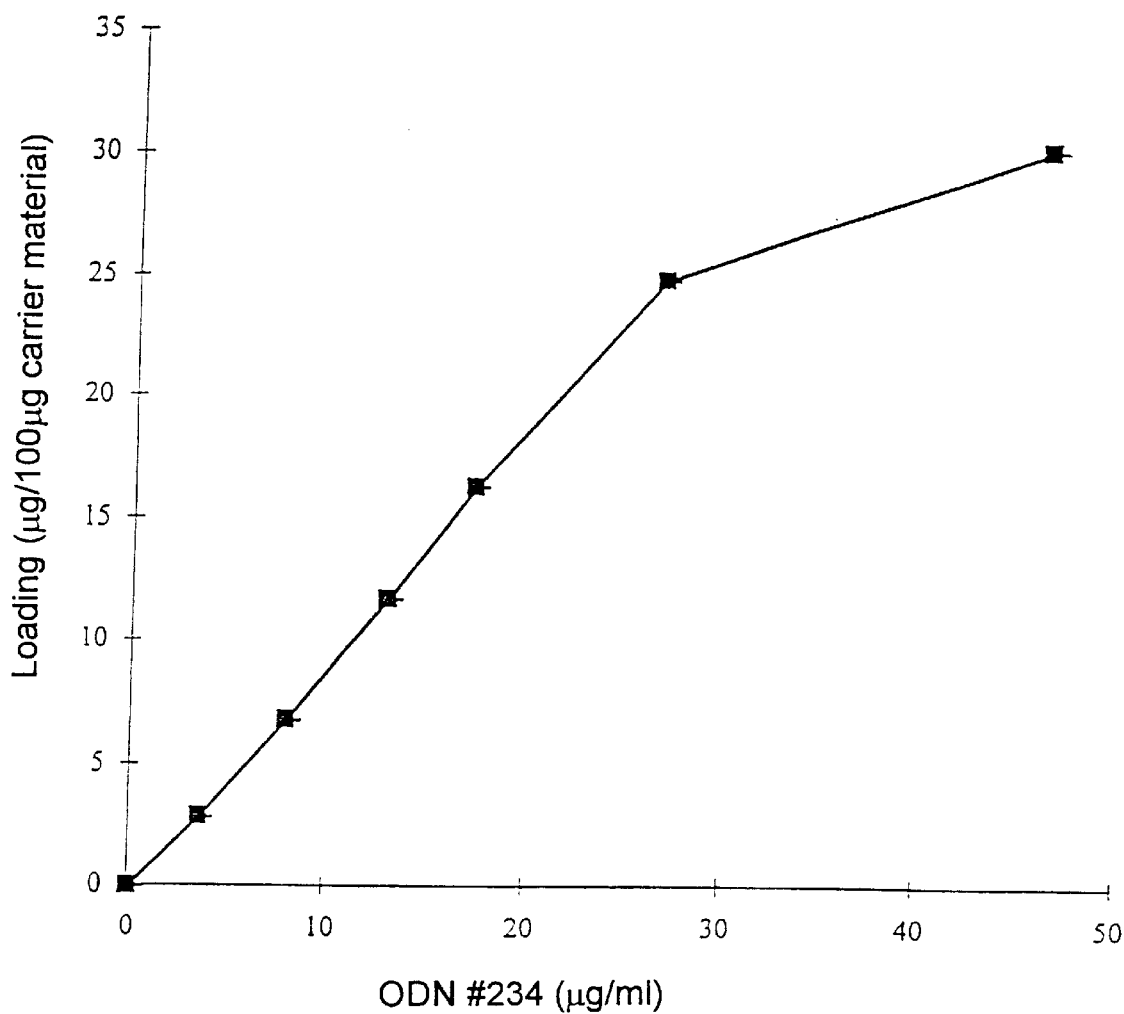
FIG. 3 is a graph showing the loading on the carrier material as a function of ODN #234 used.

To determine the bound proportion of oligonucleotide, the particle suspensions are centrifuged off in an ultracentrifuge at approximately 100,000 g in 30 minutes. The non-bound proportion is determined by HPLC analysis in the remainder (FIG. 3).

We claim:

1. A medicament in submicroscopic particulate form, comprising:

an acrylic polymer carrier material and one or more active ingredients bound to said carrier material by ionic interactions, said carrier material having the following inoalkyl acrylic ester polymer structure

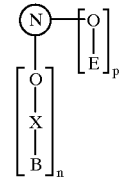

wherein N=submicroscopic particulate linear homopolymer of aminoalkyl acrylic acid or methacrylic acid ester, or copolymer thereof with acrylate or methacrylate acid or ester in a molar ratio of p:n of 0:100 to 99:1; O=oxygen of the ester group; X=branched or unbranched alkyl chain with 2 to 10 carbon atoms; B=—$NR_2$ where independently at each occurrence R=H or low alkyl; E=H or low alkyl, said carrier having a particle size distribution of 10 to 1000 nm.

2. The medicament according to claim 1, wherein said active ingredients are selected from the group consisting of nucleic acids, oligonucleotides, proteins, peptides, and biological macromolecules.

3. The medicament according to claim 1, wherein X is a branched or unbranched alkyl chain with 4 to 10 carbon atoms.

4. The medicament according to claim 1, wherein X is a linear alkyl chain with 5 to 8 carbon atoms.

5. The medicament according to claim 1, wherein X is a branched or unbranched alkyl chain with 2 or 3 carbon atoms, and a particle size distribution of 10 to 500 nm.

6. The medicament according to claim 5, wherein one or more peptide substances are bound to said carrier material.

7. The medicament according to claim 5, wherein proteins are bound to said carrier material.

8. The medicament according to claim 5, wherein biologically active macromolecules are bound to said carrier material.

9. The medicament according to claim 1, wherein b represents an ammonium group and is present in the form —$N^+R_3$, where independently at each occurrence R is H or low alkyl.

10. The medicament according to claim 1, wherein said active ingredient is selected from the group consisting of a nucleic acid, an oligonucleotide, and a peptide.

11. The medicament according to claim 1, wherein said active ingredient is a pharmaceutical.

12. The medicament according to claim 1, wherein said active ingredient is selected from the group consisting of nucleic acids and unmodified or modified oligonucleotides.

13. The medicament according to claim 1, wherein said active ingredient is selected from the group consisting of peptides, and proteins and other biologically active macromolecules.

14. The medicament according to claim 1, wherein N=submicroscopic particulate copolymer in a molar ratio of p:n of 50:50.

15. The medicament according to claim 1, where in $B=NH_2$.

16. The medicament according to claim 15 wherein N=submicroscopic particulate copolymer of aminohexyl methacrylate and methyl methacrylate.

17. The medicament according to claim 11, wherein the active ingredient is oligonucleotide.

18. The medicament according to claim 14, wherein the active ingredient is peptide TGFa.

19. A process for preparing a medicament according to claim 1 comprising the steps a) copolymerizing an acrylic acid or methacrylic acid ester having a protected aminoalkyl group and a second acrylic acid or methacrylic acid or ester, b) removing the protecting group, thereby affording a copolymer having an aminoalkyl group, c) binding said copolymer to an active ingredient by ionic interaction, and d) recovering said medicament.

20. A process according to claim 19 in which said aminoalkyl group is protected by trifluoroacetyl and the protecting group is removed by heating with this ammonia.

21. The medicament according to claim 1, wherein N=submicroscopic particulate copolymer in a molar ratio of p:n of 70:30.

* * * * *